Figure 1A:
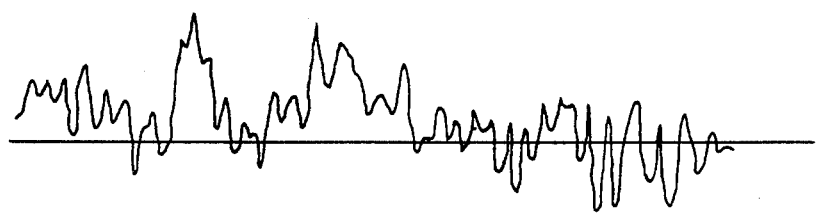
Figure 1B:
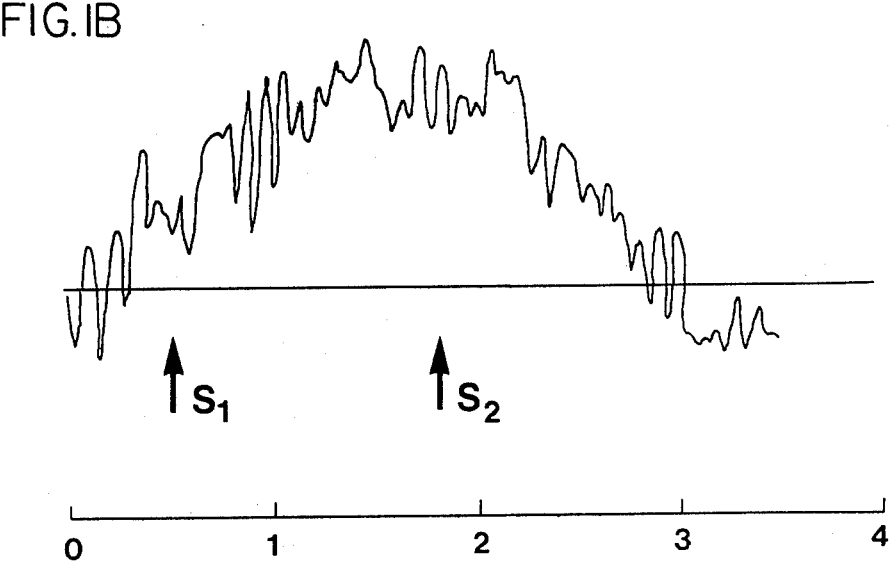

United States Patent [19]

Cavazza et al.

[11] 4,346,107
[45] Aug. 24, 1982

[54] PHARMACEUTICAL COMPOSITION COMPRISING ACYL-CARNITINE FOR THE TREATMENT OF IMPAIRED CEREBRAL METABOLISM

[75] Inventors: Claudio Cavazza, 35, Via Marocco, 00144 Rome, Italy; Menotti Calvani, Rome, Italy

[73] Assignee: Claudio Cavazza, Rome, Italy

[21] Appl. No.: 119,075

[22] Filed: Feb. 5, 1980

[30] Foreign Application Priority Data

Feb. 12, 1979 [IT] Italy ............................ 47976 A/79
Nov. 9, 1979 [IT] Italy ............................ 50795 A/79

[51] Int. Cl.³ ..................................... A61K 31/205
[52] U.S. Cl. ............................................ 424/316
[58] Field of Search ................................ 424/316

[56] References Cited

U.S. PATENT DOCUMENTS 3,793,450 2/1974 Schnell .............................. 424/343
3,810,994 5/1974 Wiegand ........................... 424/316

Primary Examiner—Stanley J. Friedman
Attorney, Agent, or Firm—Ladas & Parry

[57] ABSTRACT

A pharmaceutical composition administerable either orally or parenterally, comprising a therapeutically effective amount of an acyl-carnitine, or a pharmaceutically acceptable salt, ester or amide thereof, wherein the acyl radical is selected from the group formed by acetyl, propionyl, butyryl, hydroxybutyryl and acetoacetyl is useful in the therapeutical treatment of patients with impaired cerebral metabolism, as for instance in the states of senile and presenile psychomotor involution and in senile and presenile dementia.

3 Claims, 2 Drawing Figures

PHARMACEUTICAL COMPOSITION COMPRISING ACYL-CARNITINE FOR THE TREATMENT OF IMPAIRED CEREBRAL METABOLISM

The present invention relates to an orally or parenterally administrable pharmaceutical composition and to a therapeutic method for the treatment of patients with impaired cerebral metabolism. As known, impaired cerebral metabolism occurs in the states of senile and presenile psychomotor involution accompanied also by states of depression, in senile and presenile dementia, sequelae of cerebral stroke and cerebral ischaemias in general, or with primary impaired cerebral metabolism.

Cerebral vasodilators have been in use for some time in the treatment of states of senile and presenile psychomotor involution and particularly of senile dementia associated with cerebrovascular disorders. The use of such agents, still the prevailing object of research, is logically linked with certain observations according to which dementia is probably the result of decreased cerebral perfusion provoked by the narrowing of the lumen of the cerebral arterioles.

It would therefore appear evident to expect that drugs capable of dilating these vessels could increase cerebral blood flow thus improving the clinical picture.

Clinical practice, however, is in disagreement with such apparently logical correlations.

In Alzheimer's dementia reduced cerebral blood flow is the consequence rather than the cause of the pathological state; therefore it is highly improbable that increased blood flow can modify primary neural degeneration. In poly-infarct dementia the cerebral vessels are usually hardened and vasodilators do not appear to exert any effect. In contrast, such drugs, by acting upon peripheral vessels, withdraw blood from the brain and provoke a further reduction instead of the expected increase in cerebral perfusion.

The perplexities arising from the vasodilators currently in more general use have been very recently summarized in the British Medical Journal, No. 6189, 511–512, Sept. 1, 1979.

According to this publication, isoxuprine does not show any practical value, whereas it may decrease cerebral blood flow and its side effects include hypotension, flushing, and trembling. The effect of cyclandelate in vascular dementia has not yet been ascertained while its side effects include flushing, nausea, and rashes.

Also the "cerebral activators", viz vasodilators which appear to present an effect on cerebral metabolism by improving the utilization of oxygen and glucose in addition to their vascular action, are severely criticized by the aforementioned article in the BMJ.

Dihydroergotoxine (mesylate), although displaying negligible improvements in a wide variety of indices of mental function, gives rise to bradycardia and hypotension. Prolonged administration may lead to vascular insufficiency and gangrene of the fingers and toes.

The article concludes affirming that "on present evidence, it appears that simple vasodilators have no place in the treatment of vascular dementia. They have few demonstrable thereapeutic effects and they may be harmful. Cerebral activators are of theoretical interest."

This distrust in cerebral anti-ischaemic agents and in the currently used drugs for the treatment of senescence, particularly in those belonging to the class of "vasodilators", has also been recently pointed out in SCRIP NO. 422, Sept. 19th, 1979 p. 4, wherein it is affirmed that in regard to these drugs vasodilation or other haemodynamic properties should not be points of reference, since cerebral senescence is not a vascular condition. Therefore it cannot be stated that vasodilators are active against cerebral senescence, which implies that the prevention of cerebral senescence can no longer be an accepted claim for such drugs.

In view of the previously outlined prior art there is an evident necessity to have available new therapeutic agents for the treatment of the above pathological conditions, particularly of cerebral senescence and senile dementia. In particular, the necessity is felt for having available therapeutic agents capable of acting metabolically upon the cerebral and neural structures involved in the above pathological conditions.

In accordance with the present invention, it has been found that acyl-carnitine represented by the general formula (I)

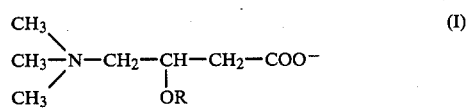

and the pharmaceutically acceptable salts, esters or amides thereof, wherein R is an acyl radical selected from the group formed by acetyl, propionyl, butyryl, hydroxybutyryl and acetoacetyl are extremely effective therapeutic agents for the treatment of impaired cerebral metabolism, senile and presenile psychomotor involution, depressive states, senile and presenile dementia, decreased cerebral blood flow, sequelae of cerebral stroke, cerebral ischaemias, and primary impaired cerebral metabolism.

Pharamaceutical compositions administerable either via the oral or parenteral route for the treatment of impaired cerebral metabolism, senile and presenile psychomotor involution, depressive states, senile and presenile dementia, decreased cerebral blood flow, sequelae of cerebral stroke, cerebral ischaemias, and primary impaired cerebral metabolism fall within the scope of the present invention and which comprise a therapeutically effective amount of an acyl-carnitine of the formula (I) or a pharmaceutically acceptable salt, ester or amide thereof, and a pharmaceutically acceptable excipient.

The fact that such compounds when administered via the oral or parenteral route are active therapeutic agents for the treatment of the aforementioned pathological conditions, is however surprising according to the results of previous studies on the interactions between acyl-carnitine (acetyl-carnitine in particular) and the nervous system.

The administration of acetyl-carnitine to animals in order to study the effects thereof on the nervous system, has already been investigated by previous Authors who however reached such conclusions as to discourage any investigation on the use thereof for the treatment of the aforementioned pathological conditions and which make the therapeutically advantageous effects obtained by the Applicant particularly surprising.

Among the more authoritative Authors, Irving B. Fritz in "Carnitine and its role in fatty acid metabolism" published in "Advances in Lipid Research" 1, 285–334 (1963) Academic Press, describes the effects of administration by injection into the rat cisterna magna under mild anaesthesia. After 3 to 5 minutes following the injection marked hyperexcitability and clonic contractions are observed, while a state of twisting-jumping persists for 5-8 minutes. Successively the animals fall into a state of depression showing little or no spontaneous activity. If prodded, they exhibit excesses of hyperexcitability followed by a return to the state of depression.

Fritz observed analogous results in the cat with a cannula inserted into the lateral ventricles of the brain. Endocerebroventricular administration of acetyl-carnitine provokes dilatation of the pupils and markedly increased motor activity.

In contrast, none of these effects were exhibited when acetyl-carnitine was given intravenously.

This leads Fritz to conclude that "it should be emphasized that acetyl-carnitine effects on neural function were not seen unless the material was injected directly into the brain. Systemic adminstration had not effects, probably because the compound could not pass the blood-brain barrier to reach higher neural structures."

An additional surprising factor in the use of acyl-carnitine (acetyl-carnitine in particular) in the aformentioned pathological states is given by the previously known relations of these substances essentially with lipid metabolism whereas it is well known that cerebral metabolism is prevailingly of the glucose type.

A therapeutic method for the treatment of impaired cerebral metabolism, senile and presenile psychomotor involution, depressive states, senile and presenile dementia, decreased cerebral blood flow, sequelae of cerebral stroke, cerebral ischaemias, and primary impaired cerebral metabolism falls within the scope of the present invention and which comprises administering either via the oral or parenteral route a therapeutically effective amount of an acyl-carnitine of the general formula (I) or a pharmaceutically acceptable salt, ester or amide thereof to patients who need such treatment.

Such a method will generally comprise oral or parenteral administration of approximately 2-20 mg/kg of bodyweight per day of acyl-carnitine of the general formula (I) or a pharmaceutically acceptable salt, ester or amide thereof, although smaller or larger doses can be administered according to the judgment of the attending physician on the basis of age, weight, general conditions and pathological situation of the treated patient.

A suitable unit dosage form for the compositions of the invention comprises from approximately 100 to approximately 1000 mg of acyl-carnitine of the formula (I) or a pharmaceutically acceptable salt, ester or amide thereof.

The effectiveness of the compounds, compositions and the therapeutic method according to the invention is supported by numerous experimental and clinical data.

Some of such clinical data is described below.

CLINICAL TRAILS

Prior to the therapeutic treatment according to the invention the patients were submitted to psychometric tests aimed at documenting the level of mental deterioration and to the recording of the contingent negative variation (CNV), slow cerebral wave closely linked to the level of alertness, attention, concentration and the capacity of motor activity.

Computerized axial tomography (CAT) was carried out on all the patients.

The patients were treated for one month with 750 mg per day (three 250-mg capsules) of acetyl-carnitine. No other therapy was used during treatment.

The psychometric and electrophysiological tests were repeated at the end of acetyl-carnitine treatment.

Detailed results referred to a group of four patients, between 58 and 67 years old, are given below.

All the patients showed improved insight. Three out of the four patients showed improved cenesthesia. Decreased emotional lability was observed in two patients.

All the patients exhibited less difficulty in maintaining attention.

From the viewpoint of self-sufficiency, two patients displayed improvements, particularly in nutrition and personal care.

In daily instrumental activity, three patients improved, particularly in the use of the telephone, domestic management and in the use of means of transport and medicines.

As regards the mental status, two patients showed improvement in recent memory and one in spatial orientation.

All the patients responded better to the symbol-number test.

It was possible to observe inclination toward greater motor activity in all the patients.

The results of the tests are tabulated in the Table.

For each patient, the values in the left column were observed prior to treatment and those in the right column after treatment.

In order to give the most objective evaluation possible of the results of the tests, activities or tests were selected wherein the subjective "sensations" of the patients played the most circumscribed role possible. Rating scales commonly accepted in psychiatrics were chosen for assessing the pre- and post-treatment conditions of the patients. The lowest score indicates normal behaviour, while the highest score corresponds to a total lack of control over the activity carried out by the patient, intermediate scores evidently correspond to degrees of control between normality and total abnormality of the activity carried out.

For instance, as far as personal cleanliness, dressing and appearance are concerned the rating scale was as follows:

1. Completely able to attend to personal cleanliness, dressing and appearance, non-incontinent.
2. Needs assistance in personal hygiene, or rarely dirties or wets himself (maximum once a week) when awake.
3. Dirties or wets himself during sleep more than once a week.
4. Dirties or wets himself when awake more than once a week.
5. No control over sphincters.

As to the daily instrumental activities, the rating scale according to M. Powell et al. (The Gerontologist, 1969, 9, 179-186) was used.

As to self-sufficiency, the rating scale according to Lowenthal, "Lives in distress" (1964) New York, Basic Books, was used.

As to the mental status, the rating scale disclosed by J. Birren in "Human Aging—A Biological and Behavioral Study" (1971), was used.

TABLE

|  | Patient 1 (58 yrs) | | Patient 2 (62 yrs) | | Patient 3 (67 yrs) | | Patient 4 (65 yrs) | |
| --- | --- | --- | --- | --- | --- | --- | --- | --- |
| Self-sufficiency | | | | | | | | |
| Personal cleanliness, dressing and appearance | 1 | 1 | 3 | 3 | 1 | 1 | 1 | 1 |
| Nutrition | 1 | 1 | 3 | 2 | 1 | 1 | 1 | 1 |
| Dress | 1 | 1 | 4 | 3 | 3 | 3 | 1 | 1 |
| Personal care | 1 | 1 | 3 | 3 | 3 | 3 | 1 | 1 |
| Walking | 2 | 2 | 3 | 3 | 3 | 2 | 1 | 1 |
| Bath | 1 | 1 | 3 | 3 | 1 | 1 | 1 | 1 |
| Daily Instrumental Activities | | | | | | | | |
| Use of telephone | 2 | 1 | 3 | 3 | 1 | 1 | 1 | 1 |
| Shopping | 2 | 2 | 4 | 4 | 3 | 3 | 2 | 2 |
| Cooking | 1 | 1 | 4 | 4 | 2 | 2 | 2 | 2 |
| Domestic management | 1 | 1 | 3 | 2 | 2 | 2 | 1 | 1 |
| Washing | 1 | 1 | 2 | 2 | 3 | 3 | 1 | 1 |
| Means of transport | 1 | 1 | 4 | 3 | 3 | 3 | 1 | 1 |
| Use of medicine | 3 | 1 | 3 | 3 | 3 | 3 | 3 | 2 |
| Use of money | 2 | 2 | 3 | 3 | 3 | 3 | 2 | 2 |
| Mental Status | | | | | | | | |
| Retention | NO | NO | NO | NO | NO | YES | NO | NO |
| Remote memory | YES | YES | YES | YES | YES | YES | NO | NO |
| Time orientation | 3 | 3 | 1 | 1 | 3 | 3 | 1 | 1 |
| Spatial orientation | 3 | 3 | 1 | 2 | 3 | 3 | 1 | 1 |
| Recent memory | YES | YES | NO | YES | YES | YES | NO | YES |
| Proverbs | NO | NO | NO | NO | YES | YES | NO | NO |
| Memory of Numbers | | | | | | | | |
| Recall of numbers in normal order | 5 | 5 | 3 | 4 | 6 | 6 | 2 | 2 |
| Recall of numbers in reverse order | 2 | 2 | 0 | 0 | 4 | 4 | 0 | 0 |
| Symbol-Number Association | improved | | improved | | improved | | improved | |
| Infantile type emotions | 3 | 3 | 1 | 1 | 6 | 6 | 2 | 2 |
| Abrupt behaviour | 2 | 0 | 1 | 1 | 4 | 4 | 1 | 1 |
| Poor emotional response | 5 | 5 | 5 | 5 | 5 | 5 | 5 | 5 |
| Lack of insight | 3 | 2 | 6 | 5 | 2 | 1 | 5 | 3 |
| Sense of Well-Being | | | | | | | | |
| Euphoria | | | | | | | | |
| Excessive laughter | 1 | 2 | 0 | 1 | 0 | 1 | 0 | 0 |
| Relevant behaviour | | | | | | | | |
| Irrelevant behaviour | | | | | | | | |
| Incoherence | 1 | 1 | 5 | 5 | 2 | 2 | 4 | 4 |
| Egoism | 0 | 0 | 0 | 0 | 6 | 6 | 6 | 5 |
| Difficulty in assimilating new experiences | 2 | 2 | 6 | 6 | 4 | 3 | 5 | 5 |
| Emotional lability | | | | | | | | |
| Changes in mood | | | | | | | | |
| Marked changes in mood | 1 | 0 | 0 | 0 | 3 | 3 | 3 | 2 |
| Occasional Emotional Incontinence | | | | | | | | |
| Linked to stimulus | 2 | 1 | 0 | 0 | 0 | 0 | 0 | 0 |
| Complains of weakness | | | | | | | | |
| Complains of feeling fatigue | | | | | | | | |
| Complains of not having the strength or will to do it | 1 | 0 | 6 | 6 | 4 | 2 | 4 | 3 |
| Confusional states | YES | YES | YES | YES | YES | YES | YES | YES |
| Delay in important replies | 2 | 2 | 5 | 5 | 1 | 1 | 6 | 6 |
| Perserverance of ideas | 1 | 1 | 2 | 2 | 4 | 4 | 4 | 3 |
| Recent memory deterioration | 6 | 5 | 6 | 6 | 4 | 4 | 6 | 5 |
| Remote memory deterioration | 0 | 0 | 0 | 0 | 1 | 1 | 6 | 4 |
| Emission of factors of fantasy into the memory | | | | | | | | |
| Frequent confabulation | | | | | | | | |
| Marked confabulation | 1 | 1 | 1 | 1 | 2 | 2 | 0 | 0 |
| Occasionally refers to the past | | | | | | | | |
| Frequently refers to the past | | | | | | | | |
| Completely absorbed by the past | 2 | 0 | 4 | 4 | 3 | 3 | 1 | 1 |
| Restless | | | | | | | | |
| Incessant activity | | | | | | | | |
| Motor activity | 1 | 0 | 4 | 3 | 4 | 3 | 5 | 3 |
| Occasionally irritable | | | | | | | | |
| Frequently irritable | | | | | | | | |
| Always irritable | 2 | 1 | 4 | 4 | 6 | 6 | 1 | 2 |
| Difficulty in maintaining attention | 4 | 3 | 6 | 4 | 2 | 1 | 5 | 4 |
| Difficulty in maintaining a task or activity | 2 | 2 | 6 | 5 | 1 | 1 | 4 | 4 |

TABLE -continued

| | Patient 1 (58 yrs) | | Patient 2 (62 yrs) | | Patient 3 (67 yrs) | | Patient 4 (65 yrs) | |
|---|---|---|---|---|---|---|---|---|
| Flight of ideas | 0 | 0 | 4 | 3 | 1 | 1 | 2 | 2 |

The CNV reading was done by means of the methods described by G. Walter in Arch. Psychiat. no. 206, 309–322, (1964). As is known, the typical experimental situation wherein the CNV formation is evoked is represented by the emission of a luminous warning stimulus in the form of a flash ($S_1$) followed by an imperative sound stimulus ($S_2$) which induce the subject to carry out a motor response (pressing a button as fast as possible).

It is furthermore known that CNV is affected by expectation, attention and motivation and that CNV is more modified in its parameters (area, maximum peak, etc.) by the memorizing capability of the subject and his personality rather than by his chronological age.

Four patients affected by presenile dementia were submitted to CNV recording prior to and after treatment with 750 mg per day per os of acetyl-carnitine for one month.

The subjects were asked to press the button whenever they heard an acute sound (7,000 Hz) over the earphones and not to press in the case of a grave sound (200 Hz).

After treatment with acetyl-carnitine improved reaction time (the subjects interrupted $S_2$ more frequently) and reduced errors in performing the motor response were observed in the four patients.

The FIGURE shows CNV tracings relative to one of the treated patients.

Tracing A is the CNV recording prior to acetyl-carnitine treatment;

Tracing B is the CNV recording after treatment.

The FIGURE shows a considerably increased maximum peak of the wave, such an event can be considered a reliable index of the increase in the CNV total area.

Although it is not intended, nor is it necessary, to be bound to any theoretical interpretation of the biochemical mechanisms which are at the basis of the activity of acyl-carnitine of the formula (I) in the therapy of the aforementioned pathological states, it may however be postulated that in cerebral ischaemic phenomena, similarly to what occurs in cardiac ischaemias, there is an accumulation of acyl-carnitine in the ischaemic tissues with consequent inhibition of adenine-nucleotide translocases, NADH-NAD dehydrogenase and acetyl-carnitine transferase.

Administration of one of the acyl-carnitines of the invention appears to provoke the reactivation of the aforementioned enzymatic systems, inducing reversibility of the pathological phenomena which occurred in the ischaemic regions, and actually regressing such phenomena until normal conditions are restored.

It must however be noted that such innovating interpretation, is still more surprising if it is observed, as already mentioned, that it was not at all predictable that the acyl-carnitines of the formula (I) were able to cross the blood-brain barrier and carry out the aforementioned functions in the neural structures.

What is claimed is:

1. A therapeutic method for the treatment of a patient affected by impaired cerebral metabolism, senile and presenile psychomotor involution, depressive states, senile and presenile dementia, decreased cerebral blood flow, sequelae of cerebral stroke, cerebral ischaemias, and primary impaired cerebral metabolism, comprising administering via the oral or parenteral route to said patient a therapeutically effective amount of an acyl-carnitine of the formula:

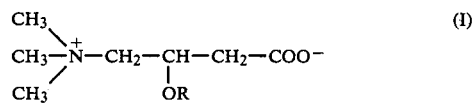

wherein R is an acyl radical selected from the group consisting of acetyl, propionyl, butyryl, hydroxybutyryl and acetoacetyl.

2. A therapeutic method according to claim 1, comprising administering to said patient via the oral or parenteral route approximately 2–20 mg/kg of body-weight/day an acyl-carnitine of the formula (I).

3. A method according to claim 1 or 2, comprising administering a pharmaceutically acceptable salt of an acyl-carnitine of formula (I).

* * * * *